United States Patent [19]

Felix et al.

[11] Patent Number: 5,084,442
[45] Date of Patent: Jan. 28, 1992

[54] CYCLIC GROWTH HORMONE RELEASING FACTOR ANALOGS AND METHOD FOR THE MANUFACTURE THEREOF

[75] Inventors: Arthur M. Felix, West Caldwell, N.J.; David C. Fry, Langhorne, Pa.; Edgar P. Heimer, Sparta; Vincent S. Madison, Mountain Lakes, both of N.J.

[73] Assignee: Hoffmann-La Roche Inc., Nutley, N.J.

[21] Appl. No.: 240,662

[22] Filed: Sep. 6, 1988

[51] Int. Cl.$^5$ .................. C07K 7/00; A61K 37/02
[52] U.S. Cl. ........................ 514/10; 514/11; 530/317; 530/318
[58] Field of Search ............ 514/9, 10, 11; 530/317, 530/318, 319, 320

[56] References Cited

U.S. PATENT DOCUMENTS 4,774,319  9/1988  Ono et al. .................... 530/324
4,959,352  9/1990  Felix ............................. 514/9

OTHER PUBLICATIONS

Campbell et al., J. Animal Sci. 67, [Suppl. 1](1989).
Campbell et al., J. Animal Sci, 66, [Suppl. 1]: 291 (1988).
Felix et al., Int. J. Peptide Protein Res., 32: 441–454 (1988).
Peptides, Structure and Function, Proceedings of the Ninth American Peptide Symposium (1985).

Primary Examiner—Jane T. Fan
Assistant Examiner—Celia Chang
Attorney, Agent, or Firm—George M. Gould; William H. Epstein; Bruce A. Pokras

[57] ABSTRACT

Linear and cyclic Growth Hormone Releasing Factor Analogs and a method for stimulating the release of Growth Hormone in subjects by administering to the subject an effective amount of the compounds of the invention.

23 Claims, No Drawings

CYCLIC GROWTH HORMONE RELEASING FACTOR ANALOGS AND METHOD FOR THE MANUFACTURE THEREOF

Growth in animals is believed to be regulated by a cascade of bio-regulatory molecules. The hypothalamus produces a substance called Growth Hormone Releasing Factor (GRF) which in turn acts upon the pituitary to cause release of growth hormone. The pituitary is maintained under negative feedback control by somatostatin and insulin growth factor (IGF). GRF has been found to be enormously active, and capable of stimulating the release of microgram per ml levels of growth hormone in the blood. GRF can be utilized therapeutically in most of the areas now considered candidates for treatment by growth hormone, for example treatment of pituitary dwarfism, diabetes resulting from growth hormone production, enhancement of wound healing, treatment of burns, retardation of the aging process, or osteoporosis or bone healing.

The successful isolation of GRF was due partly to the discovery that pancreatic tumors associated with acromegaly ectopically produced large quantities of GRF. Three forms of GRF, consisting of peptides homologous from the amino-terminus of 44, 40, and 37 amino acids, were isolated.

The 44 amino acid amidated form of GRF is considered to be the parent molecule. A wide variety of synthetic analogs have been produced. They consist of the original polypeptide or biologically active fragments thereof which exhibit various amino acid substitutions. The changes have been specifically engineered to often yield synthetic analogs with biological properties superior to those of the parent molecule. Accordingly, the desire has been to engineer GRF analogs which exhibit maximum biological activity in terms of, for example, potency, effectiveness, and stability.

To date, all of the known GRF analogs are of linear configuration. Generally, linear peptides are very flexible molecules and lack a well-defined conformation. Each amino acid in a linear peptide is exposed to the surrounding milieu resulting in greater susceptibility to enzymatic and chemical degradation.

A type of cyclic peptide (lactam) is a peptide wherein the side-chain carboxyl group of an acidic amino acid (e.g. Asp or Glu) is attached to the side-chain amino group of a basic amino acid (e.g. Lys) via the generation of an amide bond. The bonding between the two amino acids in the chain yields a cyclic (or lactam) structure.

The biological properties of cyclic peptides are often altered relative to those of their linear analogs. Cyclic peptides are much more rigid, with well-defined shapes and interior amino acid residues which are shielded from the surrounding milieu. These changes are reflected in the biological properties of the peptide. The cyclic peptides' duration of action may be longer since the compact structure renders it less susceptible to chemical and enzymatic degradation. The bio-availability of the cyclic peptide may be increased due to changes in the tissue distribution caused by the shielded interior amino acid residues. Further, the well defined conformation of the cyclic peptide will give it greater specificity for the target receptor thus reducing the probability of undesirable biological activities concomitant with the desired one. In contrast with linear peptides there are generally both central and peripheral receptors for a given linear peptide, and there may be considerable cross reactivity of a given peptide with receptors for another peptide.

SUMMARY OF THE INVENTION

The instant invention is directed to linear and cyclic analogs of GRF of the specific amino acid sequence set forth herein, including the pharmaceutically acceptable slats thereof.

The instant invention is also directed to a method of stimulating the release of growth hormone in a subject by administering to the subject an effective amount of the compounds of the invention.

The following symbols and terminology as utilized in this specification shall be defined as follows:

| | | |
|---|---|---|
| 1. | cyclic peptide | or lactam means a peptide wherein the side-chain carboxyl group of an acidic amino acid (e.g. Asp or Glu) is attached to the side-chain amino group of a basic amino acid (e.g. Lys) via the generation of an amide bond (lactam). |
| 2. | 8﹏﹏﹏12<br>A  B<br>or $cyclo^{8,12}$ | means that the eighth amino acid "A" in the peptide chain is attached to the twelfth amino acid "B" in the chain to yield a cyclic (lactam) structure. |
| 3. | 21﹏﹏﹏25<br>B  A<br>or $cyclo^{21,25}$ | means that the twenty-first amino acid "B" in the peptide chain is attached to the twenty-fifth amino acid "A" in the chain to yield a cyclic (lactam) structure. |
| 4. | $dicyclo^{8,12:21,25}$ | means that the peptide is cyclized at the 8-12 and 21-25 positions as defined above. |
| 5. | GRF | means human growth hormone releasing factor which is a polypeptide having the amino acid sequence<br><br>H—Tyr—Ala—Asp—Ala—Ile(5)—Phe—<br>Thr—Asn—Ser—Tyr(10)—Arg—Lys—<br>Val—Leu(15)—Gly—Gln—Leu—Ser—<br>Ala(20)—Arg—Lys—Leu—Leu—Gln(25)—<br>Asp—Ile—Met—Ser—Arg(30)—Gln—<br>Gln—Gly—Glu—Ser(35)—Asn—Gln—<br>Glu—Arg—Gly(40)—Ala—Arg—Ala—<br>Arg—Leu—NH₂; or<br>biologically active fragments thereof having at least the first 28 amino acids of the full polypeptide and displaying growth hormone releasing activity. |
| 7. | [Ala¹⁵]GRF | means an analog of GRF wherein an alanine residue has been substituted for the naturally occurring amino acid at position 15. Analogs of GRF are generally indicated by setting forth the substituted amino acid in brackets before the designation "GRF". |
| 8. | GRF (1-29) | means a fragment of the GRF peptide having the first 29 amino acids of the full sequence. In general, numbers in parenthesis following GRF indicate fragments of the full GRF polypeptide. |
| 9. | desNH₂Tyr¹ | means that the amino terminal NH₂ group is removed from the Tyrosine residue at position 1. |
| 10. | Ac—Tyr | means that the amino terminal NH₂ of Tyrosine is protected with an acetyl group. |

Table 1 illustrates the protocol for a typical synthetic cycle in the synthesis of the peptides of the invention.

TABLE 1

| Step | Protocol for a Typical Synthetic Cycle[a] Reagent | Time |
|---|---|---|
| 1 | 1% DMS/CH$_2$Cl$_2$ | 1 × 1 min |
| 2 | 50% TFA/CH$_2$Cl$_2$ + 1% DMS (v/v) | 1 × 1 min |
| 3 | 1% DMS/CH$_2$Cl$_2$ | 1 × 1 min |
| 4 | 50% TFA/CH$_2$Cl$_2$ + 1% DMS (v/v) | 1 × 20 min |
| 5 | CH$_2$Cl$_2$ | 3 × 1 min[b] |
| 6 | 10% DIEA/CH$_2$Cl$_2$ | 1 × 5 min |
| 7 | CH$_2$Cl$_2$ | 2 × 1 min |
| 8 | Repeat Steps 6, 7 | |
| 9 | MeOH | 2 × 1 min |
| 10 | CH$_2$Cl$_2$ | 3 × 1 min |
| 11a | 2.5 eq. Boc—AA—COOH/CH$_2$Cl$_2$ | 5 min[c] |
| b | 2.5 eq. DDC/CH$_2$Cl$_2$ | 60 min |
| c | 1.5% DIEA/CH$_2$Cl$_2$ | 15 min |
| 12 | Repeat Steps 10, 12 | |
| 13 | CH$_2$Cl$_2$ | 2 × 1 min |
| 14 | MeOH | 1 × 1 min |
| 15 | CH$_2$Cl$_2$ | 1 × 1 min[b] |

[a]Solvents for all washings and couplings were measured to volumes of 15-20 mL/g resin
[b]Kaiser ninhydrin test
[c]DMF/CH$_2$Cl$_2$ for Boc—Arg(Tos)—OH

DETAILED DESCRIPTION

The instant invention comprises cyclic peptides of the formula

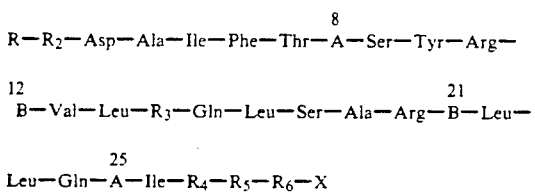

I.

wherein positions 21,25 or both positions 8,12 and 21,25 are cyclized; and

R = Tyr, desNH$_2$-Tyr, Ac-Tyr, His, N-Methyl-L-Tyr
R$_2$ = Ala, D-Ala, N-methyl-D-Ala
R$_3$ = Gly, Ala, D-Ala, Leu, Val, Ile, Nle, NVal, β-Ala, α-Aib
R$_4$ = Met, Leu, Nle, Ile
R$_5$ = Ser, Asn
R$_6$ = an amino acid sequence selected from the group consisting of Arg-Gln-Gln-Gly-Glu-Ser-Asn-Gln-Glu-Arg-Gly-Ala-Arg-Ala-Arg-Leu or fragments thereof where the fragment is reduced in number by 1 to 15 amino acids from the carboxyl and X = OH, NH$_2$,

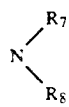

where R$_7$ and R$_8$ = H or lower alkyl
A = Asp, Asn, Glu, Gln, α-aminoadipic acid, -60-aminopimelic acid
B = Lys, Orn, diaminopropionic acid, diaminobutyric acid or their pharmaceutically acceptable salts; and the side chain carboxyl group of A may be bonded in an amide bond to the side chain amino group of B.

There are two preferred embodiments of the Formula I peptides. The first is wherein position 21,25 is cyclized yielding peptides of the formula:

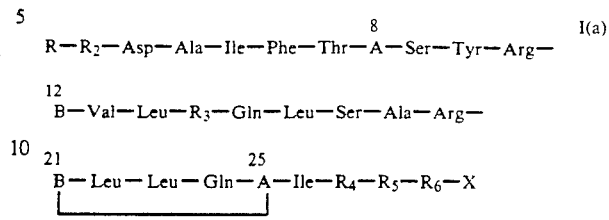

Preferred is wherein A at position 8 is Asn and B at position 12 is Lys.

Further preferred are the peptides of Formula I(a) wherein R = Tyr, desNH$_2$-Tyr, N-methyl-Tyr; R$_2$ = Ala, D-Ala; R$_3$ = Ala; and X = NH$_2$.

Even further preferred is Formula I(a) peptides as above wherein R$_4$ = Met; R$_5$ = Ser; and R$_6$ = Arg.

Particularly preferred is a Formula I(a) peptide wherein B at position 21 is Lys and A at position 25 is Asp and the side chain carboxyl group of Asp is covalently linked to the side chain main group of Lys as an amide bond.

Most particularly preferred are the following Formula I(a) peptides:

wherein R = Tyr, and R$_2$ = Ala said peptide having the formula

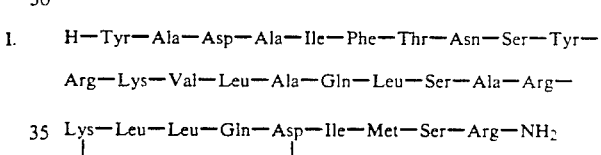

wherein R = N-methyl-Tyr and R$_2$ = D-Ala said peptide having the formula

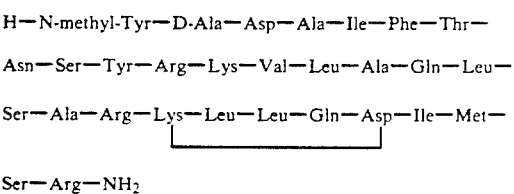

wherein R = Tyr, and R$_2$ = D-Ala said peptide having the formula

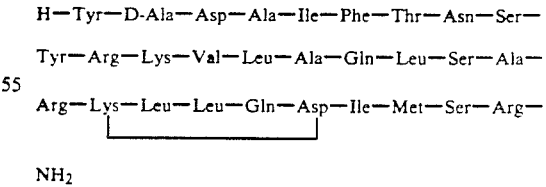

NH$_2$ wherein R = desNH$_2$Tyr and R$_2$ = Ala said peptide having the formula

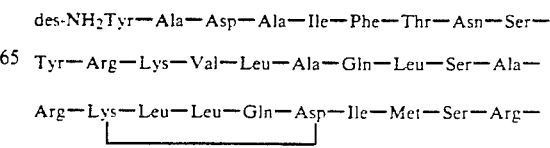

wherein R=desNH₂Tyr, and R₂=D-Ala said peptide having the formula des-NH₂—Tyr—D-Ala—Asp—Ala—Ile—Phe—Thr—Asn—

Ser—Tyr—Arg—Lys—Val—Leu—Ala—Gln—Leu—Ser—

Ala—Arg—Lys—Leu—Leu—Gln—Asp—Ile—Met—Ser—
                    └──────────────────────────┘

Arg—NH₂ wherein R=N-Me-Tyr, and R₂=Ala said peptide having the formula

H—N—Me—Tyr—Ala—Asp—Ala—Ile—Phe—Thr—Asn—

Ser—Tyr—Arg—Lys—Val—Leu—Ala—Gln—Leu—Ser—

Ala—Arg—Lys—Leu—Leu—Gln—Asp—Ile—Met—Ser—
                    └──────────────────────────┘

Arg—NH₂

The second preferred embodiment of the Formula I peptide is wherein both positions 8,12 and positions 21,25 are cyclized yielding a dicyclic peptide of the formula R—R₂—Asp—Ala—Ile—Phe—Thr—         I(b)

A—Ser—Tyr—Arg—B—Val—Leu—R₃—Gln—Leu—Ser—
└─────────────────┘

Ala—Arg—B—Leu—Leu—Gln—A—Ile—R₄—R₅—R₆—X
          └──────────────┘

Preferred are peptides of Formula I(b) wherein R=Tyr, desNH₂-Tyr, N-methyl-Tyr; R₂=Ala, D-Ala; R₃=Ala; and X=NH₂.

Further preferred are Formula I(b) peptides wherein A at position 8 =Asp and B at position 12 =Lys and B at position 21 =Lys and A at position 25 =Asp, R₃=Ala; R₄=Met; R₅=Ser; and R₆=Arg.

Particularly preferred are Formula I(b) peptides of the following formulas:

wherein R=Tyr, and R₂=Ala said peptide having the formula

H—Tyr—Ala—Asp—Ala—Ile—Phe—Thr—

Asp—Ser—Tyr—Arg—Lys—Val—Leu—Ala—Gln—Leu—
└───────────────────┘

Ser—Ala—Arg—Lys—Leu—Leu—Gln—Asp—Ile—Met—
              └──────────────────────┘

Ser—Arg—NH₂ wherein R=N-methyl-Tyr and R₂=D-Ala said peptide having the formula

H—N-methyl-Tyr—D-Ala—Ile—Phe—Thr—

Asp—Ser—Tyr—Arg—Lys—Val—Leu—Ala—Gln—Leu—
└───────────────────┘

Ser—Ala—Arg—Lys—Leu—Leu—Gln—Asp—Ile—Met—
              └──────────────────────┘

Ser—Arg—NH₂ wherein R=Tyr, and R₂=D-Ala said peptide having the formula

H—Tyr—D-Ala—Ile—Phe—Thr—

Asp—Ser—Tyr—Arg—Lys—Val—Leu—Ala—Gln—Leu—
└───────────────────┘

Ser—Ala—Arg—Lys—Leu—Leu—Gln—Asp—Ile—Met—
              └──────────────────────┘

Ser—Arg—NH₂.

wherein R=desNH₂Tyr, and R₂=Ala said peptide having the formula des-NH₂—Tyr—Ala—Ile—Phe—Thr—

Asp—Ser—Tyr—Arg—Lys—Val—Leu—Ala—Gln—Leu—
└───────────────────┘

Ser—Ala—Arg—Lys—Leu—Leu—Gln—Asp—Ile—Met—
              └──────────────────────┘

Ser—Arg—NH₂.

wherein R=desNH₂Tyr and R₂=D-Ala said peptide having the formula des-NH₂—Tyr—D-Ala—Ile—Phe—Thr—

Asp—Ser—Tyr—Arg—Lys—Val—Leu—Ala—Gln—Leu—
└───────────────────┘

Ser—Ala—Arg—Lys—Leu—Leu—Gln—Asp—Ile—Met—
              └──────────────────────┘

Ser—Arg—NH₂.

wherein R=N-Me-Tyr, and R₂=D-Ala said peptide having the formula

H—N—Me—Tyr—Ala—Ile—Phe—Thr—

Asp—Ser—Tyr—Arg—Lys—Val—Leu—Ala—Gln—Leu—
└───────────────────┘

Ser—Ala—Arg—Lys—Leu—Leu—Gln—Asp—Ile—Met—
              └──────────────────────┘

Ser—Arg—NH₂.

The instant invention also comprises linear peptides of the above set forth amino acid sequences.

The peptides are synthesized by a suitable method such as by exclusive solid phase synthesis, partial solid phase methods, by fragment condensation or by classical solution synthesis. Recombinant DNA techniques can also be used for those analogs containing only natural amino acid residues. The peptides are preferably prepared by solid phase peptide synthesis as described by Merrifield, J. Am. Chem. Soc. 85, 2149 (1963). The synthesis is carried out with amino acids that are protected at the alpha-amino-terminus. Trifunctional amino acids with labile side-chains are also protected with suitable groups which will prevent a chemical reaction from occurring at that site during the assemblage of the peptide. The alpha-amino protecting group is selectively removed to allow subsequent coupling reactions to take place at the amino-terminus. The conditions for the removal of the alpha-amino protecting group do not cause deprotection of the side-chain protecting groups.

The alpha-amino protecting groups are those known to be useful in the art of stepwise synthesis of peptides. Included are acyl type protecting groups (e.g. formyl, trifluoroacetyl, acetyl), aromatic urethane type protecting groups (e.g. benzyloxycarboyl (Cbz) and substituted benzyloxycarbonyl), alphatic urethane protecting groups (e.g. t-butyloxycarbonyl (Boc), isoprpyloxycarbonyl, cyclohexyloxycarbonyl) and alkyl type protecting groups (e.g. benzyl, triphenylmethyl). The preferred protecting group is Boc. The side-chain protecting groups for Tyr include tetrahydropyranyl, tert.-butyl, trityl, benzyl, Cbz, Z-Br-Cbz and 2,5-dichlorobenzyl. The preferred side-chain protecting group for Tyr is 2,6-dichlorobenzyl. The side-chain protecting groups for Asp include benzyl, 2,6-dichlorobenzyl, methyl, ethyl and cyclohexyl. The preferred side-chain protecting group for Asp is cyclohexyl. The side-chain protecting groups for Thr and Ser include acetyl, benzoyl, trityl, tetrahydropyranyl, benzyl, 2,6-dichlorobenzyl and Cbz. The preferred protection group for Thr and Ser is benzyl. The side-chain protecting groups for Arg include nitro, Tosyl (Tos), Cbz, adamantyloxycarbonyl mesitoylsulfonyl (Mts) or Boc. The preferred protecting group for Arg is Tos. The side-chain amino group of Lys may be protected with Cbz, 2-chlorobenzyloxycarbonyl (2-Cl-Cbz) 2-bromobenzyloxycarbonyl (2-BrCbz), Tos or Boc. The 2-Cl-Cbz is the preferred protecting groups for Lys. The selection of the side-chain protecting groups is based on the following: The side-chain protecting group remains intact during coupling and is not split off during the deprotection of the amino-terminus protecting group or during coupling conditions. The side-chain protecting group must be removable upon the completion of the synthesis of the final peptide and using reaction conditions that will not alter the target peptide.

Solid phase synthesis is usually carried out from the carboxyl-terminus by coupling the alpha-amino protected (side-chain protected) amino acid to a suitable solid support. An ester linkage is formed when the attachment is made to a chloromethylated or hydroxymethyl resin and the resultant target peptide will have a free carboxyl group at the C-terminus. Alternatively, a benzyhydrylamine or p-methylbenzhydrylamine resin is used in which case an amide bond is formed and the resultant target peptide will have a carboxamide group at the C-terminus. These resins are commercially available and their preparation is described by Stewart et al., "Solid Phase Peptide Synthesis" (2nd Edition, Pierce Chemical Co., Rockford, IL., 1984).

The C-terminal amino acid, Arg, protected at the side-chain with (Tos) and at the alpha-amino function with Boc is coupled to the benzyhydrylamine resin using various activating agents including dicyclohexylcarbodiimide (DCC), N,N'-diisopropylcarbodiimide carbonyldiimidazole or benzotriazol-1-yl-oxy-tris (dimethylamino)phosphonium hexafluorophosphate (BOP). Following the attachment to the resin support the alpha-amino protecting group is removed by using trifluoroacetyl acid (TFA) or HCl in dioxane at a temperature between 0° and 25°. Dimethylsulfide is added to the TFA after the introduction of methionine (Met) to suppress possible S-alkylation. After removal of the alpha-amino protecting group the remaining protected amino acids are coupled stepwise in the required order to obtain the desired peptide sequence. Various activating agents can be used for the coupling reactions including DCC, N,N'-diisopropylcarbodiimide, benzotriazol-1-yl-oxy-tris-(dimethylamino)-phosphonium hexafluorophosphate (BOP) and DCC-hydroxybenzotriazole (HOBt). Each protected amino acid is used in excess (>2.5 equivalents) and the couplings are usually carried out in dimethylformamide (DMF), $CH_2Cl_2$ or mixtures thereof. The extent of completion of the coupling reaction is monitored at each stage by the ninhydrin reaction as described by Kaiser et al., Anal. Biochem., 34, 595 (1970). In cases where incomplete coupling is determined the coupling reaction is repeated. The coupling reactions can be performed automatically on a Vega 250, Applied Biosystems synthesizer or other commercially available instrument. After the entire assemblage of the target peptide the peptide-resin is deprotected with TFA/dithioethane and then reacted with a reagent such as liquid HF for 1–2 hours at 0° which cleaves the peptide from the resin and removes all side-chain protecting groups.

Side-chain to side-chain cyclization on the solid support requires the use of an orthogonal protection scheme which enables selective cleavage of the side-chain functions of acidic amino acids (e.g. Asp) and the basic amino acid (e.g. Lys). The 9-fluorenylmethyl (OFm) protecting group for the side-chain of Asp and the 9-fluorenylmethoxycarbonyl (Fmoc) protecting group for the side-chain of Lys can be used for this purpose. In these cases the side-chain protecting groups (OFm and Fmoc) of the Boc-protected peptide-resin are selectively removed with piperidine in DMF. Cyclization is achieved on the solid support using various activating agents including DCC, DCC/HOBt or BOP. The HF reaction is carried out on the cyclized peptide-resin as described above.

Purification of the poylpeptides of the invention can be effected using procedures well known in peptide chemistry. The subject poylpeptides may be purified using preparative hplc; however, other known chromatographic procedures such as gel permeation, ion exchange and partition chromatography or countercurrent distribution can also be employed.

The instant invention also comprises a method of stimulating the release of growth hormone in a subject by administering to the subject an effective amount of the Formula I peptides.

The poylpeptides of this invention have growth hormone releasing activity. Pharmaceutically compositions in accordance with the invention include analogs of about 29 to 44 amino acids in length, or a nontoxic salt of any of these, dispersed in a pharmaceutically or veterinarily acceptable liquid or solid carrier. Such pharmaceutical compositions can be used for therapeutic or diagnostic purposes in clinical medicine, both human and veterinary. For example, they are useful in the treatment of growth-related disorders such as hypopituitary dwarfism and diabetes resulting from abnormalities in growth hormone production or for the improvement of bone, wound, or burn healing, or osteoporosis. Furthermore, they can also be used to stimulate the growth or enhance feed efficiency of animals raised for meat production to improve the quality of meat production, or to enhance milk production and stimulate egg production.

Appropriate dosages of the poylpeptides of the invention to be administered will vary somewhat depending on the individual subject and the condition being treated. The skilled worker will be able to determine appropriate dosages based on the known circulating levels of growth hormone associated with normal growth and the growth hormones releasing activity of the polypeptide.

As is well known in the art, treatment of growth-related disorders will necessitate varying dosages from individual to individual depending upon the degree of insufficiency of growth hormone production. generally, a dosage range of from 0.04 μg/kg/day to about 20.0 μg/kg/day based on body weight of the subject may be used to stimulate release of growth hormone. The dosages employed to stimulate growth activity in livestock will be significantly higher (per kg. of subject weight) than the dosages employed to restore normal growth in cases of growth hormone deficiencies such as pituitary dwarfism in humans. In livestock generally a dosage in the range of from 0.4 μg/kg/day to about 100 μg/kg/day subcutaneously may be used to stimulate release of pituitary growth hormone.

Thus, there is provided in accordance with this invention a method of treating growth-related disorders characterized by insufficient production of growth hormone which comprises administering an amount of the analogs of this invention sufficient to stimulate the production of growth hormone to levels associated with normal growth.

Normal levels of growth hormone vary considerably among individuals and, for any given individual, levels of circulating growth hormone vary considerably during the course of a day. In adult humans, normal serum levels of growth hormone have been reported to vary from about 0–10 nanograms/ml. In children, normal serum levels of growth hormone have been reported to vary from about 0–20 nanograms/ml.

In order to treat hypopituitary dwarfism effectively with the described analogs, treatment is administered during the period of normal growth. In females, this period generally does not extend far beyond the onset of menses. Thus, treatment of females should be effected approximately from the ages of 12 to 16 years, depending upon the individual. In males, the stimulation of growth may be possible for a considerably longer period of time beyond puberty. Thus, effective treatment of males will normally be possible up to about 18 to 19 years of age and, in some individual cases, up to about 25 years.

There is also provided a method of increasing the growth rate of animals by administering an amount of the analog sufficient to stimulate the production of growth hormone at a level greater than that associated with normal growth.

The poylpeptides of the invention can be administered in the form of human or veterinary pharmaceutical compositions which can be prepared by conventional pharmaceutical formulation techniques. Compositions suitable for oral, intravenous, subcutaneous, intramuscular, intraperitoneal intranasal, intraocular, buccal, or transdermal administration may be employed. A suitable dosage form for pharmaceutical use is from about 0.01 to about 0.5 mg of the compound of the invention, which may be lyophilized for reconstitution with sterile water or saline. The composition should be maintained at a pH below about 5.0 in order to maintain the stability of the analog. Serum albumin from the species being treated (e.g. human serum albumin in the case of humans, bovine serum albumin in the case of cows and so forth) may also be present together with other known pharmaceutical adjuvants.

The present invention will be described in connection with the following examples which are set forth for the purposes of illustration only.

EXAMPLE 1

Synthesis of Cyclo$^{21,25}$[Ala$^{15}$]-GRF(1-29)-NH$_2$

Preparation of
Boc-[Ala$^{15}$]-Cyclo$^{21-25}$-GRF(3-29)-Benzhydrylamine-resin

The Boc-Arg(Tos)-BHA-resin (9.5 g, 0.348 meq/g, 3.31 meq) was deprotected and neutralized according to the protocol described in FIG. 1. A portion of intermediate, Boc-GRF (26-29)-BHA-resin (3.36 g, 0.975 mmol) was removed and stepwise solid phase synthesis continued as described above for 5 cycles of solid phase synthesis including the use of Boc-Asp$^{25}$ (OFm)-OH and Boc-Lys$^{21}$(Fmoc)-OH to give Boc-[Lys$^{21}$(Fmoc), Asp$^{25}$-(OFm)]-GRF(21-29)-BHA-resin. This intermediate was deprotected with 20% piperidine/DMF for 20 min to give Boc-[Lys$^{21}$, Asp$^{25}$]-GRF(21-29)-BHA-resin which was cyclized by reaction with BOP reagent (1.37 g, 2.93 mmol, 3 eq) in DMF (50 mL) containing diisopropylethylamine (DIEA) (1.02 mL, 5.86 mmol, 6 eq) for 2 hours. After washing, cyclization was repeated two more times for 12 hours and 3 hours, respectively (negative Kaiser ninhydrin test). Solid phase synthesis continued for an additional 8 cycles to give 4.60 g (0.975 mmol) of Boc-[Ala$^{15}$]-Cyclo$^{21,25}$-GRF(13-29)-BHA-resin. A portion (1.0 g, 0.212 mmol) was subjected to 10 additional cycles of solid phase synthesis to give 1.15 g of Boc-[Ala$^{15}$]-Cyclo$^{21,25}$-GRF(13-29)-BHA-resin.

Following the assemblage of Boc-[Ala$^{15}$]-Cyclo$^{21,25}$-GRF (3-29)-BHA-resin, a portion (0.57 g, 0.106 mmol) was subjected to 2 final cycles of solid phase synthesis with Boc-Ala-OH and Boc-Tyr(2,6-Cl$_2$Bzl)-OH as outlined in FIG. 1. The peptide-resin was cleaved with hydrogen fluoride (HF) (approx. 10 mL) containing 1-propanethiol (1.62 mL) at 0° for 2 hours. Evaporation of HF was followed by washing with Ethyl acetate (EtOAc), extraction with TRF (4×10 mL), evaporation and trituration with ether to give 187.4 mg of crude product.

The crude product (187.4 mg) was dissolved in 10 mL of 0.025% TFA/H$_2$O, stirred, filtered and applied on (2) Synchropak RP-P columns 1.0 cm×25 cm each. Eluant: (A) H$_2$O (0.25% TFA)—(B) ACN (0.025% TFA); linear gradient, 20%–45% (B) in 120 min; flow rate 2 mL/min. Fractions were collected at 1 min intervals. Fractions 47–49 were pooled and lyophilized to give 3.0 mg of semi-pure product.

The semi-pure product (3.0 mg) was repurified on a Nucleosil C-18 column (1.0 cm×50 cm; 5μ). Eluant: (A) H$_2$O (0.1% TFA), (B) ACN (0.1% TFA); linear gradient, 20%–40% (B) in 120 min; flow rate 3 mL/min. Fractions were collected at 1 min intervals. Fractions 113–114 were pooled and lyophilized to give 0.8 mg of product that was determined to be homogeneous by analytic hplc. Confirmation of structure was provided by Fast Atom Bombardment (FAB) mass spectroscopy. Calcd. 3354.9; Found: 3354.2. Confirmation of sequence was provided by sequence analysis which also confirmed the lactam at position 21-25.

EXAMPLE 2

Synthesis of Cyclo$^{21,21}$[N-MethylTyr$^1$, D-Ala$^2$, Ala$^{15}$]-GRF(1-29)-NH$_2$ A second portion of Boc-[Ala$^{15}$]-Cyclo$^{21,25}$-GRF(3-29)-BHA-resin (0.70 g, 0.166 mol) was subjected to a final 2 cycles of solid phase synthesis using Boc-D-Ala-OH and Boc-N-methyl-L-Tyr(2,6-Cl$_2$Bzl)-OH as outlined in FIG. 1. The peptide-resin was cleaved with HF (approx. 10 mL) containing 1-propanethiol (2.1 mL) at 0° for 2 hours. Evaporation of HF was followed by washing with EtOAc, extraction with TFA (4×10 mL), evaporation and trituration with ether to give 180 mg of crude product.

The crude product (180 mg) was dissolved in 5 mL of H$_2$O (0.025% TFA), stirred, centrifuged, filtered and applied on (2) Synchropak RP-P columns (1×25 cm each). Eluant: (A) H$_2$O (0.25% TFA)—(B) ACN (0.025% TFA); linear gradient, 20%–45% (B) in 120 min; flow rate 2 mL/min. Fractions were collected at 1 min interval (2 mL/tube). Fractions 49–51 were pooled and lyophilized to give 5.6 mg of semi-pure product.

The semi-pure product (5.6 mg) was repurified on a Nucleosil C-18 column as described in Example 1. Fractions 109–110 were pooled and lyophilized to give 1.11 mg of product that was determined to be homogeneous by analytic hplc. Confirmation of structure was provided by FAB mass spectroscopy. Calcd. 3368.9; Found: 3367.9.

EXAMPLE 3

Synthesis of Cyclo$^{21,25}$[D-Ala$^2$, Ala$^{15}$]-GRF(1-29)-NH$_2$

Another portion of Boc-[Ala$^{15}$]-Cyclo$^{21,25}$-GRF(3-29)-BHA-resin (1.0 g, 0.136 mmol) was subjected to a final 2 cycles of solid phase synthesis using Boc-D-Ala-OH and Boc-Tyr(2,6-Cl$_2$Bzl)-OH as outlined in FIG. 2. The peptide-resin was cleaved with HF (approx. 10 mL) containing 1-propanethiol (3 mL) for 2 hours at 0°. Evaporation of HF was followed by washing with EtOAc, extraction with TFA (4×10 mL), evaporation and trituration with ether to give 403 mg of crude product. Purification was carried out by reversed phase hplc using the same general procedure described in Example 1. The product was determined to be homogeneous by analytic hplc. Confirmation of structure was provided by FAB Mass Spectroscopy. Calcd. 3354.9; Found: 3354.9. Amino Acid Anal. (6 M HCl, 110°, 24 h): Asp, 2.67; Thr, 0.90; Ser, 2.72; Glu, 2.02; Ala, 4.00; Val, 0.90; Met, 0.90; Ile, 1.78; Leu, 3.82; Tyr, 1.77; Phe, 0.83; Lys, 1.76; Arg, 2.77.

EXAMPLE 4

Synthesis of Cyclo$^{21,25}$[N-MeTyr$^1$, Ala$^{15}$]-GRF(1-29)-NH$_2$

Another portion of Boc-[Ala$^{15}$]-cyclo$^{21,25}$-GRF(3-29)-BHA-resin (1.0 g, 0.136 mmol) was subjected to a final 2 cycles of solid phase synthesis using Boc-Ala-OH and Boc-N-MeTyr(2,6-Cl$_2$Bzl)-OH as outlined in FIG. 1. The peptide-resin was cleaved with HF (approx. 10 mL) containing propanethiol (3 mL) for 2 hours at 0°. Evaporation of HF was followed by washing with EtOAc, extraction with TFA (4×10 mL), evaporation and trituration with ether to give 222 mg of crude product. Purification was carried out by reversed phase hplc using the same general procedure described in Example 1. The product was determined to be homogeneous by analytic hplc. Confirmation of structure was provided by FAB Mass Spectroscopy. Calcd. 3368.9; Found: 3368.9. Amino Acid Anal. (6 M HCl, 110°, 72 h): Asp, 3.08; Thr, 1.05; Ser, 3.25; Glu, 2.32; Ala, 4.45; Val, 0.63; Met, 1.00; Ile, 1.59; Leu, 4.04; Tyr, 1.11; Phe, 0.61; Lys, 1.60; Arg, 310.

EXAMPLE 5

Synthesis of Cyclo$^{21,25}$[desNH$_2$Tyr$^1$,Ala$^{15}$]-GRF(1-29)-NH$_2$

Another portion of Boc-[Ala$^{15}$]-Cyclo$^{21,25}$-GRF(3-29)-BHA-resin (1.0 g, 0.136 mmol) was subjected to a final 2 cycles of solid phase synthesis using Boc-Ala-OH and desNH$_2$-Tyr-OH as outlined in FIG. 1. The peptide-resin was cleaved with HF (approx. 10 mL) containing propanethiol (3 mL) for 2 hours at 0°. Evaporation of HF was followed by washing with EtOAc, extraction with TFA (4×10 mL), evaporation and trituration to give 208 mg of crude product. Purification by reversed phase hplc using the same procedure described in Example 1 gave product that was homogeneous by analytic hplc. Confirmation of structure was provided by FAB Mass Spectroscopy. Calcd. 3339.9; Found: 3340.3.

EXAMPLE 6

Synthesis of Cyclo$^{21,25}$[desNH$_2$Tyr$^1$,D-Ala$^2$,Ala$^{15}$]-GRF(1-29)-NH$_2$ Another portion of Boc-[Ala$^{15}$]-cyclo$^{8,12}$-GRF(3-29)-BHA-resin (1.0 g, 0.136 mmol) was subjected to a final 2 cycles of solid phase synthesis using Boc-D-Ala-OH and desNH$_2$-Tyr-OH as outlined in FIG. 2. The peptide-resin was cleaved with HF (approx. 10 mL) containing propanethiol (3 mL) for 2 hours at 0°. Evaporation of HF was followed by washing with EtOAc, extraction with TFA (4×10 mL), evaporation and trituration to give 432 mg of crude product. Purification by reversed phase hplc using the same procedure described in Example 1 gave product that was homogeneous by analytic hplc. Confirmation of structure was provided by FAB Mass Spectroscopy. Calcd. 3339.9; Found: 3339.0.

EXAMPLE 7

Synthesis of Cyclo$^{8,12;21,25}$[Asp$^8$, Ala$^{15}$]-GRF(1-29)-NH$_2$

Preparation of Boc-[Asp$^8$Ala$^{15}$]-Cyclo$^{8,12;21,25}$-GRF(3-29)-Benzhydrylamine-resin A portion of intermediate Boc[Ala$^{15}$]-Cyclo$^{21,25}$-GRF (13-29)-BHA-resin (2.50 g, 0.53 mmol) was subjected to 5 cycles solid phase synthesis including the use of Boc-Lys$^{12}$ (Fmoc)-OH and Boc-Asp$^8$(OFm)-OH to give 2.92 g of Boc-[Asp$^8$(OFm), Lys$^{12}$-(Fmoc), Ala$^{15}$]-Cyclo$^{21,25}$-GRF(8-29)-BHA-resin. A portion (1.95 g, 0.053 mmol) was deprotected with 20% piperidine/DMF for 20 min to give Boc-[Asp$^8$,Lys$^{12}$, Ala$^{15}$]-Cyclo$^{21,25}$-GRF(8-29)-BHA-resin which was cyclized by reaction with BOP reagent (469 mg, 1.06 mmol, 3 eq) in DMF (40 mL) containing diisopropylethylamine (0.37 mL, 2.12 mmol, 6 eq) for 4 hours. After washing, cyclization was repeated two more times for 17 hours and 6 hours, respectively (negative Kaiser Ninhydrin Test). Solid phase synthesis continued for an additional 5 cycles to give approx. 2 g of Boc-[Asp$^8$, Ala$^{15}$]-Cyclo$^{8,12;21,25}$-GRF(3-29)-benzhydrylamine-resin.

Following the assemblage of Boc-[Asp$^8$,Ala$^{15}$]-Cyclo$^{8,12;21,25}$-GRF (3-29)-BHA-resin, a portion (1.0 g, 0.177 mmol) was subjected to 2 final cycles of solid phase synthesis with Boc-Ala-OH and Boc-Tyr(2,6-Cl$_2$Bzl)-OH as outlined in FIG. 1. A portion (0.52 g, 0.088 mmol) was cleaved with HF (approx. 10 mL) containing 1-propanethiol (1.56 mL) at 0° for 2 hours. Evaporation of HF was followed by washing with EtOAc, extraction with TRF (4×10 mL), evaporation and trituration with ether to give 99.8 mg of crude product.

The crude product (99.8 mg) was dissolved in 10 mL of 0.025% TFA/H$_2$O and purified as in Example 1. Fractions 80-82 were pooled and evaporated and were purified on a Nucleosil C-18 column as in Example 1. Fraction 145-146 were pooled and lyophilized to give 0.65 mg of product that was determined to be homogeneous by analytic hplc. Confirmation of structure was provided by FAB mass spectroscopy. Calcd. 3337.9; Found: 3337.9. Additional confirmation of sequence was provided by sequence analysis which confirmed the lactams at positions 21-25 and 8-12.

EXAMPLE 8

Synthesis of Cyclo$^{8,12;21,25}$[N-MethylTyr$^1$,D-Ala$^2$, Asp$^8$, Ala$^{15}$]-GRF(1-29)-NH$_2$ A second portion of Boc-[Asp$^8$, Ala$^{15}$]-Cyclo$^{8,12;21,25}$ GRF(3-29)-BHA-resin (1.0 g, 0.177 mmol) was subjected to 2 final cycles of solid phase synthesis with Boc-D-Ala-OH and Boc-N-methyl-L-Tyr(2,6-Cl$_2$Bzl)-OH as outlined in FIG. 1. A portion (0.53 g, 0.888 mmol) was cleaved with HF (approx. 10 mL) containing 1-propanethiol (1.59 mL) at 0° for 2 hours. Evaporation of HF was followed by washing with EtOAc, extraction with TFA (4×10 mL), evaporation and trituration with ether to give 101.8 mg of crude product.

A total of 200.7 mg of crude product was dissolved in 10 mL of H$_2$O (0.0025% TFA) stirred, centrifuged, filtered and applied on (2) Synchropak RP-P columns 1.0×25 cm each). Eluant: (A) H$_2$O (0.0025% TFA)—(B) ACN (0.0025% TFA); linear gradient, 20%-45% (B) in 120 min; flow rate 2 mL/min. Fractions were collected at 1 min intervals (2 mL/tube). Fractions 75-76 were pooled and lyophilized to give 3.4 mg of semi-pure product.

The semi-pure product (3.4 mg) was repurified on a Nucleosil C-18 as described in Example 1. Fractions 122-123 were pooled and lyophilized to give 0.58 mg of product that was determined to be homogeneous by hplc. Confirmation of structure was provided by FAB mass spectroscopy. Calcd. 3352.9; Found: 3352.2. Amino acid analysis (6 M HCl, 110°, 24 h): Asp, 2.8; Thr, 0.9; Ser, 2.9; Glu, 2.5; Ala, 3.4; Val, 1,1; Met, 1.2; Ile, 2.1; Leu, 4.9; Phe, 1.0; Lys, 1.7; Arg, 3.6.

EXAMPLE 9

Synthesis of Cyclo$^{8,12;21,25}$[D-Ala$^2$, Asp$^8$,Ala$^{15}$]-GRF(1-29)-NH$_2$ Another portion of Boc-[Asp$^8$Ala$^{15}$]-cyclo$^{8,12,21,25}$-GRF (3-29)-BHA-resin (1 g, 0.14 mmol) was subjected to a final 2 cycles of solid phase synthesis using Boc-D-Ala-OH and Boc-Tyr(2,6-Cl$_2$Bzl)-OH as outlined in FIG. 1. The peptide-resin was cleaved with HF (approx. 10 mL) containing propanethiol (3 mL) for 2 hours at 0°. Evaporation of HF was followed by washing with EtOAc, extraction with TFA (4×10 mL), evaporation and trituration with ether to give 431 mg of crude product. Purification by reversed phase hplc using the same procedure described in Example 7 gave product that was homogeneous by analytic hplc. Confirmation of structure was provided by FAB Mass Spectroscopy. Calcd. 3337.9; Found: 3337.2.

EXAMPLE 10

Synthesis of Cyclo$^{8,12;21,25}$[N-MeTyr$^1$, Asp$^8$,Ala$^{15}$]-GRF (1-29)-NH$_2$ Another portion of Boc-[Asp$^8$,Ala$^{15}$]-cyclo$^{8,12;21,25}$-GRF(3-29)-BHA-resin (1 g, 0.14 mol) was subjected to a final 2 cycles of solid phase synthesis using Boc-Ala-OH and Boc-N-MeTyr(2,6-Cl$_2$Bzl)-OH as outlined in FIG. 1. The peptide-resin was cleaved with HF (approx. 10 mL) containing propanethiol (3 mL) for 2 hours at 0°. Evaporation of HF was followed by washing with EtOAc, extraction with TFA (4×10 mL), evaporation and trituration with ether to give 386 mg of crude product. Purification by reversed phase hplc using the same procedure as described in Example 7 1 gave product that was homogeneous by analytic hplc. Confirmation of structure was provided by FAB Mass Spectroscopy. Calcd. 3352.0; Found: 3351.5.

EXAMPLE 11

Synthesis of Cyclo$^{8,12;21,25}$[desNH$_2$Tyr$^1$,Asp$^8$,Ala$^{15}$]-GRF(1-29)-NH$_2$ Another portion of Boc-[Asp$^8$,Ala$^{15}$]-cyclo$^{8,12;21,25}$-GRF(3-29)-BHA-resin (1 g, 0.14 mol) was subjected to a final 2 cycles of solid phase synthesis using Boc-Ala-OH and desNH$_2$-Tyr-OH as outlined in FIG. 2. The peptide-resin was cleaved with HF (approx. 10 mL) containing propanethiol (3 mL) for 2 hours at 0°. Evaporation of HF was followed by washing with EtOAc, extraction with TFA (4×10 mL), evaporation and trituration with ether to give 403 mg of crude product. Purification by reversed phase hplc using the same procedure described in Example 7 gave product that was homogeneous by analytic hplc. Confirmation of structure was provided by FAB Mass Spectroscopy. Calcd. 3322.9; Found: 3322.2.

EXAMPLE 12

Synthesis of Cyclo$^{8,12;21,25}$[desNH$_2$Tyr$^1$,D-Ala$^2$,Asp$^8$Ala$^{15}$]-GRF(1-29)-NH$_2$ Another portion of Boc-[Asp$^8$,Ala$^{15}$]-cyclo$^{8,12;21,25}$-GRF(3-29)-BHA-resin (1.0 g, 0.14 mol) was subjected to a final 2 cycles of solid phase synthesis using Boc-D-Ala-OH and desNH$_2$-Tyr-OH as outlined in FIG. 1. The peptide-resin was cleaved with HF (approx. 10 mL) containing propanethiol (2.1 mL) for 2 hours. Evaporation of HF was followed by washing with EtOAc, extraction with TFA (4×10 mL), evaporation and trituration with ether to give 430 mg of crude product. Purification by reversed phase hplc using the same procedure described in Example 7 gave product that was homogeneous by analytic hplc. Confirmation of structure was provided by FAB Mass Spectroscopy. Calcd. 3322.9; Found: 3323.0.

EXAMPLE 13

Synthesis of [Asp$^8$,Ala$^{15}$]-GRF(1-29)-NH$_2$

In a separate synthesis starting with Boc-Arg(Tos)-BHA resin (see example 1) the solid phase assemblage was carried out as described above to give Boc-[Asp-$^8$(OFm) Lys$^{21}$(Fmoc)-Ala$^{15}$]-GRF (1-29)BHA-resin. 1 g portion of the resin (0.26 mmol) was deprotected with 20% piperidine/DMF for 20 min to give Boc-[Asp$^8$, Ala$^{15}$]-GRF (1-29)-BHA-resin. The partially protected peptide resin was cleaved with HF as in example 2 to give 117 mg of crude product.

The crude product (117 mg) was dissolved in 8 mL of H$_2$O (containing 0.0025% TFA) filtered and applied on (2) Synchropak RP-P columns 1×25 cm each). Eluant: (A) H$_2$O (0.0025% TFA)—(B) ACN (0.0025% TFA); linear gradient, 20%–45% (B) in 120 min; flow rate 2 mL/min. Fractions were collected at 1 min intervals. Fractions 74-80 were pooled and lyophilized to give 16 mg of semi-pure product.

The semi-pure product (16 mg) was dissolved in water (approx. 3 mL) and repurified on a Nucleosil C-$_{18}$ column (1×50 cm). Eluant: (A) H$_2$O (0.25% TFA). (B) ACN (0.025% TFA); linear gradient, 20%–45% (B) in 120 min; flow rate 2.5 mL/min. Fractions were collected at 1 min intervals 25 mL/fractions. Fractions 92, 94-97 were pooled and lyophilized to give 6.6 mg of product. Amino acid analysis (6 M HCl, 110°, 24 h): Asp, 3.04; Thr, 0.95; Ser, 2.81; Glu, 2.11; Ala, 4.16; Val, 0.98; Met, 0.96; Ile, 1.9; Leu, 4.13; Tyr, 2.03; Phe, 0.92; Lys, 1.95; Arg, 3.09.

EXAMPLE 14

In Vitro (Cell Dispersion) Assay of GRF

Pituitaries from 30–40 male Sprague-Dawley rats (175 g) were removed aseptically after decapitation. The anterior lobes were collected, washed 3 times in sterile Hepes buffer (0.025 M) (pH 7.35) and dispersed at 37° in 20-30 ml Hepes buffer (pH 7.35) containing collagenase (4 mg per ml) and Dispase (Protease grade II, 2 mg per ml). After gentle 100-110 min vortexing and trituration by Pasteur pipette, the dispersed cells were separated by centrifugation (150×g, 4 min) and re-suspended in Hepes buffer containing neuraminidase (8 g/ml), and 200 g/ml ethylenediaminetetraacetic acid (EDTA) disodium salt, pH 7.35, for 10 min.

The cells were washed twice with plating medium and plated on multiwell-plates (1.5×10$^5$ cells per ml) using the following defined medium: F-12/DMEM/BGJ (6:3:1) (Gibco: 430–1700/430–1600/3-20-2591) with 2 g BSA/1., 2.38 g Hepes/1.50 mg PSN antibiotic mixture (Gibco Laboratories), 10 mg/l transferring (Sigma T2252) with 1.83 g NaHCO$_3$/l (Baker 3506). The medium in each well was supplemented either with a sample of the novel GRF peptide or natural GRF(1-44)-NH$_2$ at concentrations ranging from 0.8 to 200 fmol per ml of medium. Control wells contained no supplement. Plating was done with this medium added with 2% fetal calf serum to ensure rapid fixation of the cells.

On the fourth day, the cells were washed twice with the defined medium without fetal calf serum. Finally, 900 μl of defined medium was added to each well plus 100 μl of the same medium containing each individual treatment, in triplicate. After 4 hours of incubation the medium was collected and diluted as required to conduct radioimmunoassay (RIAs) for rat growth hormone.

RIAs for rat growth hormone were conducted using Sinha's anti-murine GH immune serum and procedures according to the National Pituitary Agency using protein A to precipitate antibody antigen complex. The results are summarized in Table 2.

TABLE 2

RELATIVE POTENCIES OF CYCLIC$^{21,25}$ and Cyclic$^{8,12,21,25}$ Analogs of GRF(1-29)—NH$_2$

| GRF ANALOG | RELATIVE POTENCY |
|---|---|
| GRF(1-29)—NH$_2$ | 0.8 |
| GRF(1-44)—NH$_2$ | 1.0 |
| Cyclo$^{21,25}$—[Ala$^{15}$]—GRF(1-29)—NH$_2$ | 1.27 |
| Cyclo$^{21,25}$—[D—Ala$^2$,Ala$^{15}$]—GRF(1-29)—NH$_2$ | 1.99 |
| Cyclo$^{21,25}$—[N—MeTyr$^1$, D—Ala$^2$,Ala$^{15}$]—GRF (1-29)—NH$_2$ | 1.92 |
| Cyclo$^{21,25}$—[desNH$_2$Tyr$^1$,Ala$^{15}$]—GRF (1-29)—NH$_2$ | 1.47 |
| Cyclo$^{8,12;21,25}$[Asp$^8$,Ala$^{15}$]GRF(1-29)—NH$_2$ | 2.24 |
| Cyclo$^{8,12;21,25}$[N—MethylTyr$^1$,D—Ala$^2$,Asp$^8$, Ala$^{15}$]—GRF(1-29)—NH$_2$ | 0.61 |
| [Asp$^8$,Ala$^{15}$]GRF(1-29)—NH$_2$ | 0.79 |

While the invention has been described in connection with the preferred embodiment, it is not intended to limit the scope of the invention to the particular form set forth, but, on the contrary it is intended to cover such alternatives, modifications, and equivalents as may be included within the spirit and scope of the invention as defined by the appended claims.

We claim:

1. A cyclic peptide of the formula

R—R$_2$—Asp—Ala—Ile—Phe—Thr—A—Ser—Tyr—Arg—

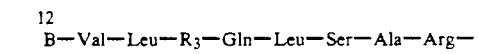

B—Val—Leu—R$_3$—Gln—Leu—Ser—Ala—Arg—

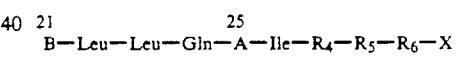

B—Leu—Leu—Gln—A—Ile—R$_4$—R$_5$—R$_6$—X wherein positions 21,25 or both positions 8,12 and 12,25 are cyclized; and R = Tyr, desNH$_2$-Tyr, Ac-Tyr, His, N-Methyl-L-Tyr
R$_2$ = Ala, D-Ala, N-methyl-D-Ala
R$_3$ = Gly, Ala, Leu, Val, Ile, Nle, NVal, β-Ala, α-Aib
R$_4$ = Met, Leu, Nle, Ile
R$_5$ = Ser, Asn
R$_6$ = an amino acid sequence selected from the group consisting of Arg-Gln-Gln-Gly-Glu-Ser-Asn-Gln-Glu-Arg-Gly-Ala-Arg-Ala-Arg-Leu or fragments thereof where the fragment is reduced in number by 1 to 15 amino acids from the carboxyl end
X = OH, NH$_2$,

where R$_7$ and R$_8$ = H or lower alkyl
A = Asp, Asn, Glu, Gln, α-aminoadipic acid, -60 -aminopimelic acid
B = Lys, Orn, diaminopropionic acid, diaminobutyric acid or their pharmaceutically acceptable salts; wherein the cyclic bonding of 21,25 or both 8,12, and 21,25 are amide bonds via condensation of the free carboxyl group of A may be bonded and the free amino group of B.

2. The peptide of claim 1 which is cyclized at the 21,25 position having the formula R—R₂—Asp—Ala—Ile—Phe—Thr—A⁸—Ser—Tyr—Arg— I(a)

¹²B—Val—Leu—R₃

²¹Gln—Leu—Ser—Ala—Arg—B—Leu—Leu—Gln—A²⁵—Ile—

R₄—R₅—R₆—X.

3. The peptide of claim 2 wherein A at position 8 is Asn and B at position 12 is Lys.

4. The peptide of claim 3 wherein R=Tyr, desNH₂-Tyr, or N-methyl-Tyr; R₂=Ala, D-Ala; R₃=Ala; and X=NH₂.

5. The peptide of claim 4 wherein R₄=Met; R₅=Ser; and R₆=Arg.

6. The peptide of claim 5 wherein B at position 21 is Lys and A at position 25 is Asp and the side chain carboxyl group of Asp is covalently linked to the side amino group of Lys as an amide bond.

7. The peptide of claim 6 wherein R=Tyr and R₂=Ala said peptide having the formula H—Tyr—Ala—Asp—Ala—Ile—Phe—Thr—Asn⁸—Ser—

¹²Tyr—Arg—Lys—Val—Leu—Ala—Gln—Leu—Ser—Ala—

²¹Arg—Lys—Leu—Leu—Gln—Asp²⁵—Ile—

Met—Ser—Arg—NH₂.

8. The peptide of claim 6 wherein R=N-methyl-Tyr and R₂=D-Ala said peptide having the formula H—N-Methyl-L-Tyr—D-Ala—Asp—Ala—Ile—Phe—

⁸Thr—Asn—Ser—Tyr—Arg—Lys—Val—Leu—D-Ala—¹²

Gln—Leu—Ser—Ala—Arg—

Lys—Leu—Leu—Gln—Asp—Ile—Met—Ser—Arg—NH₂.

9. The peptide of claim 6 wherein R=Tyr and R₂=D-Ala said peptide having the formula H—Tyr—D-Ala—Asp—Ala—Ile—Phe—Thr—Asn—

Ser—Tyr—Arg—Lys—Val—Leu—Ala—Gln—Leu—Ser—

Ala—Arg—Lys—Leu—Leu—Gln—Asp—Ile—

Met—Ser—Arg—NH₂.

10. The peptide of claim 6 wherein R=desNH₂Tyr and R₂=Ala said peptide having the formula desNH₂Tyr—Ala—Asp—Ala—Ile—Phe—Thr—Asn—Ser—

Tyr—Arg—Lys—Val—Leu—Ala—Gln—Leu—Ser—Ala—

Arg—Lys—Leu—Leu—Gln—Asp—Ile—Met—Ser—

Arg—NH₂.

11. The peptide of claim 6 wherein R=desNH₂Tyr and R₂=D-Ala said peptide having the formula des-NH₂—Tyr—D-Ala—Asp—Ala—Ile—Phe—Thr—Asn—

Ser—Tyr—Arg—Lys—Val—Leu—Ala—Gln—Leu—Ser—

Ala—Arg—Lys—Leu—Leu—Gln—Asp—Ile—Met—

Ser—Arg—NH₂.

12. The peptide of claim 6 wherein R=N-Methyl-Tyr, and R₂=Ala said peptide having the formula H—N—Me—Tyr—Ala—Asp—Ala—Ile—Phe—Thr—Asn—

Ser—Tyr—Arg—Lys—Val—Leu—Ala—Gln—Leu—Ser—

Ala—Arg—Lys—Leu—Leu—Gln—Asp—Ile—Met—

Ser—Arg—NH₂.

13. The peptide of claim 1 which is cyclized at the 8,12 and 21,25 positions having the formula R—R₂—Asp—Ala—Ile—Phe— I(b)

⁸Thr—A—Ser—Tyr—Arg—B¹²—Val—Leu—R₃

Gln—Leu—Ser—Ala—

²¹Arg—B—Leu—Leu—Gln—A²⁵—Ile—R₄—R₅—R₆—X.

14. The peptide of claim 13 wherein R=Tyr, desNH₂-Tyr, or N-methylTyr; R₂=Ala, D-Ala; R₃=Ala; and X=NH₂.

15. The peptide of claim 14 wherein A at position 8 =Asp and B at position 12 =Lys, and B at position 21 =Lys and A at position 25 =Asp; R₄=Met; R₅=Ser; and R₆=Arg.

16. The peptide of claim 15 wherein R=Tyr and R₂=Ala said peptide having the formula H—Tyr—Ala—Asp—Ala—Ile—Phe—

Thr—Asp—Ser—Tyr—Arg—Lys—Val—Leu—Ala—Gln—

Leu—Ser—Ala—Arg—Lys—Leu—Leu—Gln—Asp—Ile—

Met—Ser—Arg—NH₂.

17. The peptide of claim 15 wherein R=N-methyl-Tyr and R₂=D-Ala said peptide having the formula H—N—Me—Tyr—D-Ala—Asp—Ala—Ile—Phe—

Thr—Asp—Ser—Tyr—Arg—Lys—Tyr—Arg—Lys—Val—
       |_____|

Leu—Ala—Gln—Leu—Ser—Ala—Arg—

Lys—Leu—Leu—Gln—Asp—Ile—Met—Ser—Arg—NH$_2$.
|_____|

18. The peptide of claim 15 wherein R=Tyr, and R$_2$=D-Ala said peptide having the formula H—Tyr—D-Ala—Ile—Phe—Thr—

Asp—Ser—Tyr—Arg—Lys—Val—Leu—Ala—Gln—Leu—
|_____|

Ser—Ala—Arg—Lys—Leu—Leu—Gln—Asp—Ile—
       |_____|

Met—Ser—Arg—NH$_2$.

19. The peptide of claim 15 wherein R=desNH$_2$Tyr and R$_2$=Ala said peptide having the formula desNH$_2$Tyr—Ala—Ile—Phe—Thr—

Asp—Ser—Tyr—Arg—Lys—Val—Leu—Ala—Gln—Leu—
|_____|

Ser—Ala—Arg—Lys—Leu—Leu—Gln—Asp—Ile—
       |_____|

Met—Ser—Arg—NH$_2$.

20. The peptide of claim 15 wherein R=desNH$_2$Tyr and R$_2$=D-Ala said peptide having the formula desNH$_2$Tyr—D-Ala—Ile—Phe—Thr—

Asp—Ser—Tyr—Arg—Lys—Val—Leu—Ala—Gln—Leu—
|_____|

Ser—Ala—Arg—Lys—Leu—Leu—Gln—Asp—Ile—Met—
       |_____|

Ser—Arg—NH$_2$.

21. The peptide of claim 15 wherein R=N-Me-Tyr, and R$_2$=D-Ala said peptide having the formula H—NMeTyr—Ala—Ile—Phe—Thr—

Asp—Ser—Tyr—Arg—Lys—Val—Leu—Ala—Gln—Leu—
|_____|

Ser—Ala—Arg—Lys—Leu—Leu—Gln—Asp—Ile—
       |_____|

Met—Ser—Arg—NH$_2$.

22. A method of stimulating the release of growth hormone in a subject which comprises administering to said subject an effective amount of a peptide of the formula $$R-R_2-Asp-Ala-Ile-Phe-Thr-\overset{8}{A}-Ser-Tyr-Arg-$$

$$\overset{12}{B}-Val-Leu-R_3-Gln-Leu-Ser-Ala-Arg-$$

$$\overset{21}{B}-Leu-Leu-Gln-A-Ile-\overset{25}{R_4}-R_5-R_6-X$$

wherein positions 21,25 or both positions 8,12 and 21,25 are cyclized; and
R=Tyr, desNH$_2$-Tyr, Ac-Tyr, His, N-Methyl-L-Tyr
R$_2$=Ala, D-Ala, N-metyl-D-Ala
R$_3$ =Gly, Ala, Leu, Val, Ile, Nle, NVal, β-Ala, α-Aib
R$_4$=Met, Leu, Nle, Ile
R$_5$=Ser, Asn
R$_6$=an amino acid sequence selected from the group consisting of Arg-Gln-Gln-Gly-Glu-Ser-Asn-Gln-Glu-Arg-Gly-Ala-Arg-Ala-Arg-Leu or fragments thereof where the fragment is reduced in number by 1 to 15 amino acids from the carboxyl end
X=OH, NH$_2$,

where R$_7$ and R$_8$ =H or lower alkyl
A=Asp, Asn, Glu, Gln, α-aminoadipic acid, -60 -aminopimelic acid
B=Lys, Orn, diaminopropionic acid, diaminobutyric acid or the pharmaceutically acceptable salts.

23. The method of claim 22 wherein the compound is administered orally, intravenously, intranasally, parenterally, intraocularly, buccally, or transdermally.

* * * * *

UNITED STATES PATENT AND TRADEMARK OFFICE
CERTIFICATE OF CORRECTION

PATENT NO. : 5,084,442

DATED : January 28, 1992

INVENTOR(S) : Arthur Felix, David Fry, Edgar Heimer and Vincent Madison

It is certified that error appears in the above-identified patent and that said Letters Patent is hereby corrected as shown below:

In claim 1, column 16, line 64, "A= Asp, Asn, Glu, Gln, α-aminoadipic acid, -60-aminopimelic acid" should be
-- A= Asp, Asn, Glu, Gln α-aminopimelic acid, α-aminoadipic acid --

In claim 1, column 17, line 2 "group of A may be bonded and the free amino group of B" should be -- group of A and the free amino group of B --

In claim 21, column 19, line 53 "The peptide of claim 15 wherein R=N-Me-Tyr, and $R_2$=D-Ala " should be -- The compound of claim 15 wherein R=NMe-Tyr and $R_2$=Ala --

In claim 22, column 20, line 46 " A=Asp, Asn Glu, Gln, α-aminoadipic acid, -60 - aminopimelic acid should be
-- A=Asp, Asn, Glu, Gln, α-aminopimelic acid, α-aminoadipic acid --

Signed and Sealed this

Twenty-second Day of February, 1994

Attest:

BRUCE LEHMAN

Attesting Officer

Commissioner of Patents and Trademarks